United States Patent
Carrano et al.

(10) Patent No.: US 7,302,033 B2
(45) Date of Patent: Nov. 27, 2007

(54) IMAGING GEOMETRY FOR IMAGE-GUIDED RADIOSURGERY

(75) Inventors: Aaron W. Carrano, San Jose, CA (US); Gopinath Kuduvalli, San Jose, CA (US); Michael J. Saracen, Oakland, CA (US); Mohan Bodduluri, Palo Alto, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 11/170,832

(22) Filed: Jun. 29, 2005

(65) Prior Publication Data

US 2007/0003007 A1  Jan. 4, 2007

(51) Int. Cl.
*A61B 6/02* (2006.01)
(52) U.S. Cl. ................................. 378/41
(58) Field of Classification Search .......... 378/41, 378/65, 68, 92, 62, 195, 197, 205
See application file for complete search history.

(56) References Cited

U.S. PATENT DOCUMENTS

| | | | |
|---|---|---|---|
| 5,068,882 A | 11/1991 | Eberhard | |
| 5,375,156 A | 12/1994 | Kuo-Petravic et al. | |
| 6,094,472 A | 7/2000 | Smith | |
| 6,104,780 A * | 8/2000 | Hanover et al. | 378/92 |
| 6,198,790 B1 | 3/2001 | Pflaum | |
| 6,307,914 B1 | 10/2001 | Kunieda et al. | |
| 6,618,464 B2 | 9/2003 | Mizobuchi et al. | |
| 6,842,502 B2 * | 1/2005 | Jaffray et al. | 378/65 |
| 6,876,719 B2 | 4/2005 | Ozaki | |
| 2003/0048868 A1 * | 3/2003 | Bailey et al. | 378/65 |
| 2004/0017888 A1 | 1/2004 | Seppi et al. | |
| 2004/0228442 A1 | 11/2004 | Sakaguchi et al. | |
| 2005/0105680 A1 | 5/2005 | Nabors et al. | |

FOREIGN PATENT DOCUMENTS

WO  WO2004/061477  7/2004

OTHER PUBLICATIONS

PCT Search Report mailed Feb. 16, 2007, PCT/US06/25794, filed Jun. 29, 2006.
PCT Written Opinion of the International Searching Authority mailed Feb. 16, 2007, PCT/US06/25794, filed Jun. 29, 2006.

* cited by examiner

*Primary Examiner*—Edward J. Glick
*Assistant Examiner*—Anastasia S. Midkiff
(74) *Attorney, Agent, or Firm*—Blakely, Sokoloff, Taylor & Zafman LLP

(57) ABSTRACT

A system and method for stereoscopically imaging a patient at multiple locations in a radiation treatment system with a variable imaging geometry to enable the delivery of radiation treatments from multiple ranges of treatment angles without obstructing the imaging system or the radiation treatment.

48 Claims, 16 Drawing Sheets

IMAGING GEOMETRY FOR IMAGE-GUIDED RADIOSURGERY

TECHNICAL FIELD

The present invention relates generally to image-guided radiation treatment systems and, in particular, to the geometry of imaging systems for guiding radiation treatment.

BACKGROUND

Radiosurgery and radiotherapy are radiation treatment systems that use external radiation beams to treat pathological anatomies (e.g., tumors, lesions, vascular malformations, nerve disorders, etc.) by delivering a prescribed dose of radiation (e.g., X-rays or gamma rays) to the pathological anatomy while minimizing radiation exposure to surrounding tissue and critical anatomical structures (e.g., the spinal chord). Both radiosurgery and radiotherapy are designed to necrotize pathological anatomy while sparing healthy tissue and the critical structures. Radiotherapy is characterized by a low radiation dose per treatment and many treatments (e.g., 30 to 45 days of treatment). Radiosurgery is characterized by a relatively high radiation dose in one, or at most a few, treatments. In both radiotherapy and radiosurgery, the radiation dose is delivered to the site of the pathological anatomy from multiple angles. As the angle of each radiation beam is different, each beam intersects a target region occupied by the pathological anatomy, but passes through different areas of healthy tissue on its way to and from the target region. As a result, the cumulative radiation dose in the target region is high and the average radiation dose to healthy tissue and critical structures is low.

Frame-based radiotherapy and radiosurgery treatment systems employ a rigid, invasive stereotactic frame to immobilize a patient during pre-treatment imaging for diagnosis and treatment-planning (e.g., using a CT scan or other 3-D imaging modality, such as MRI or PET), and also during subsequent radiation treatments. These systems are limited to intracranial treatments because the rigid frame must be attached to bony structures that have a fixed spatial relationship with target region, and the skull and brain are the only anatomical features that satisfy that criterion.

In one type of frame-based radiosurgery system, a distributed radiation source (e.g., a cobalt 60 gamma ray source) is used to produce an approximately hemispherical distribution of simultaneous radiation beams though holes in a beam-forming assembly. The axes of the radiation beams are angled to intersect at a single point (treatment isocenter) and the beams together form an approximately spherical locus of high intensity radiation. The distributed radiation source requires heavy shielding, and as a result the equipment is heavy and immobile. Therefore, the system is limited to a single treatment isocenter.

In another type of frame-based radiotherapy system, known as intensity modulated radiation therapy (IMRT), the radiation treatment source is an x-ray beam device (e.g., a linear accelerator) mounted in a gantry structure that rotates around the patient in a fixed plane of rotation. IMRT refers to the ability to shape the cross-sectional intensity of the radiation beam as it is moved around the patient, using multi-leaf collimators (to block portions of the beam) or compensator blocks (to attenuate portions of the beam). The axis of each beam intersects the center of rotation (the treatment isocenter) to deliver a dose distribution to the target region. Because the center of rotation of the gantry does not move, this type of system is also limited to a single treatment isocenter.

Image-guided radiotherapy and radiosurgery systems (together, image-guided radiation treatment (IGRT) systems) eliminate the need for invasive frame fixation by tracking changes in patient position between the pre-treatment imaging phase and the treatment delivery phase (in-treatment phase). This correction is accomplished by acquiring real-time stereoscopic X-ray images during the treatment delivery phase and registering them with reference images, known as digitally reconstructed radiograms (DRRs), rendered from a pre-treatment CAT scan. A DRR is a synthetic X-ray produced by combining data from CAT scan slices and computing a two-dimensional (2-D) projection through the slices that approximates the geometry of the real-time imaging system.

Gantry-based IGRT systems add an imaging x-ray source and a detector to the treatment system, located in the rotational plane of the LINAC (offset from the LINAC, e.g., by 90 degrees), and which rotate with the LINAC. The imaging x-ray beam passes through the same isocenter as the treatment beam, so the imaging isocenter coincides with the treatment isocenter, and both isocenters are fixed in space.

FIG. 1 illustrates the configuration of an image-guided, robotic-based radiation treatment system 100, such as the CyberKnife® Radiosurgery System manufactured by Accuray, Inc. of California. In this system, the trajectories of the treatment x-ray beams are independent of the location of the imaging x-ray beams. In FIG. 1, the radiation treatment source is a LINAC 101 mounted on the end of a robotic arm 102 having multiple (e.g., 5 or more) degrees of freedom in order to position the LINAC 101 to irradiate a pathological anatomy (target region or volume) with beams delivered from many angles, in many planes, in an operating volume around the patient. Treatment may involve beam paths with a single isocenter, multiple isocenters, or with a non-isocentric approach (i.e., the beams need only intersect with the pathological target volume and do not necessarily converge on a single point, or isocenter, within the target).

In FIG. 1, the imaging system includes X-ray sources 103A and 103B and X-ray detectors (imagers) 104A and 104B. Typically, the two x-ray sources 103A and 103B are mounted in fixed positions on the ceiling of an operating room and are aligned to project imaging x-ray beams from two different angular positions (e.g., separated by 90 degrees) to intersect at a machine isocenter 105 (where the patient will be located during treatment on a treatment couch 106) and to illuminate imaging surfaces (e.g., amorphous silicon detectors) of respective detectors 104A and 104B after passing through the patient. FIG. 2 illustrates the geometry of radiation treatment system 100. Typically, the x-ray detectors 104A and 104B are mounted on the floor 109 of the operating room at ninety degrees relative to each other and perpendicular to the axes 107A and 107B of their respective imaging x-ray beams. This orthogonal, stereoscopic imaging geometry is capable of great precision, reducing registration errors to sub-millimeter levels. However, there are some inherent limitations associated with this imaging geometry when installed in a typical operating room, which may have a ceiling no more than nine or ten feet high.

As illustrated in FIG. 2, the LINAC 101 is highly maneuverable and relatively compact, but it still requires a minimum amount of separation between the patient 108 and the ceiling 110 of the operating room to deliver treatments from above the patient. There are also certain positions that the LINAC may be unable to occupy, either because the LINAC may block one of the imaging x-ray beams or because one of the x-ray detectors may block the radiation treatment beam. Furthermore, because the patient must be located at least some minimum distance from the ceiling to enable access from above, there may be insufficient room below the patient to deliver treatment from below, even if treatment from under the patient would be more beneficial (e.g., treating the spinal area while the patient is laying face up). Therefore, the location of the imaging center of the imaging system may need to be chosen as a compromise between treatment access and imaging access.

BRIEF DESCRIPTION OF THE FIGURES

The present invention is illustrated by way of example, and not by limitation, in the figures of the accompanying drawings in which:

FIG. 3C illustrates another application of the embodiment of FIG. 3A;

DETAILED DESCRIPTION

Apparatus and methods for imaging geometry in radiation treatment systems are described. In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "coupled" as used herein, may mean directly coupled or indirectly coupled through one or more intervening components or systems. The term "X-Ray image" as used herein may mean a visible X-ray image (e.g., displayed on a video screen) or a digital representation of an X-ray image (e.g., a file corresponding to the pixel output of an X-ray detector). The terms "in-treatment image" or "real-time image" as used herein may refer to images captured at any point in time during a treatment delivery phase of a radiosurgery or radiotherapy procedure, which may include times when the radiation source is either on or off. The term IGR as used herein may refer to image-guided radiation therapy, image-guided radiosurgery, or both.

Figure 1:
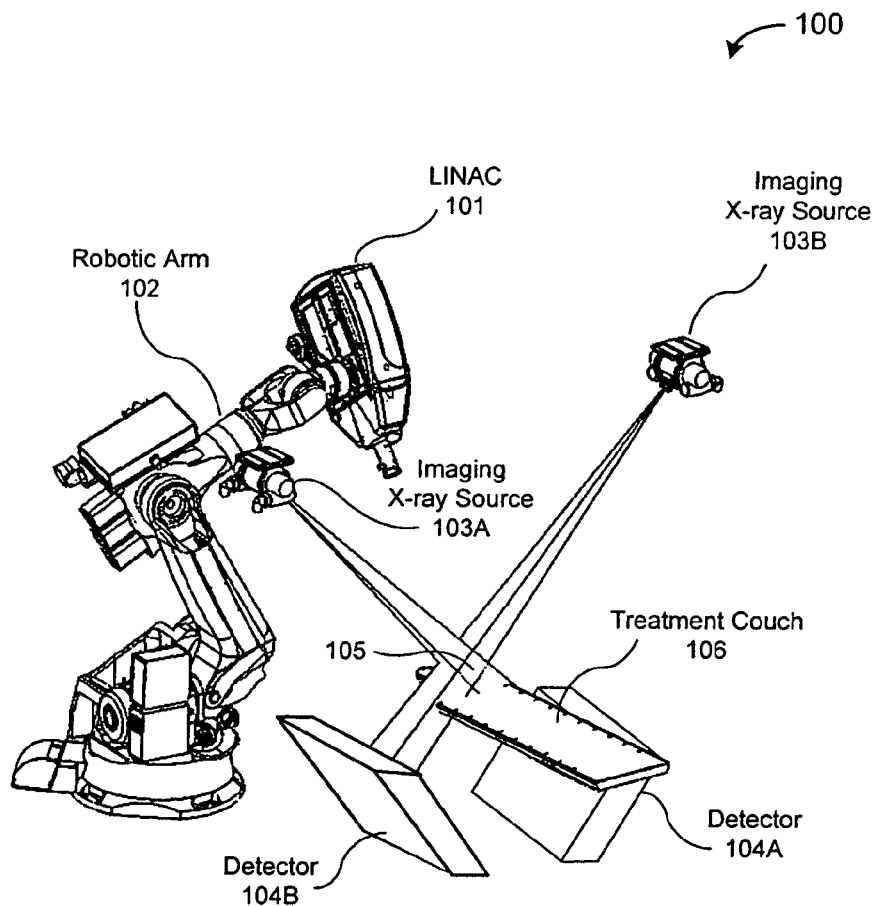
FIG. 1 illustrates a conventional image-guided radiation treatment system.
Figure 2:
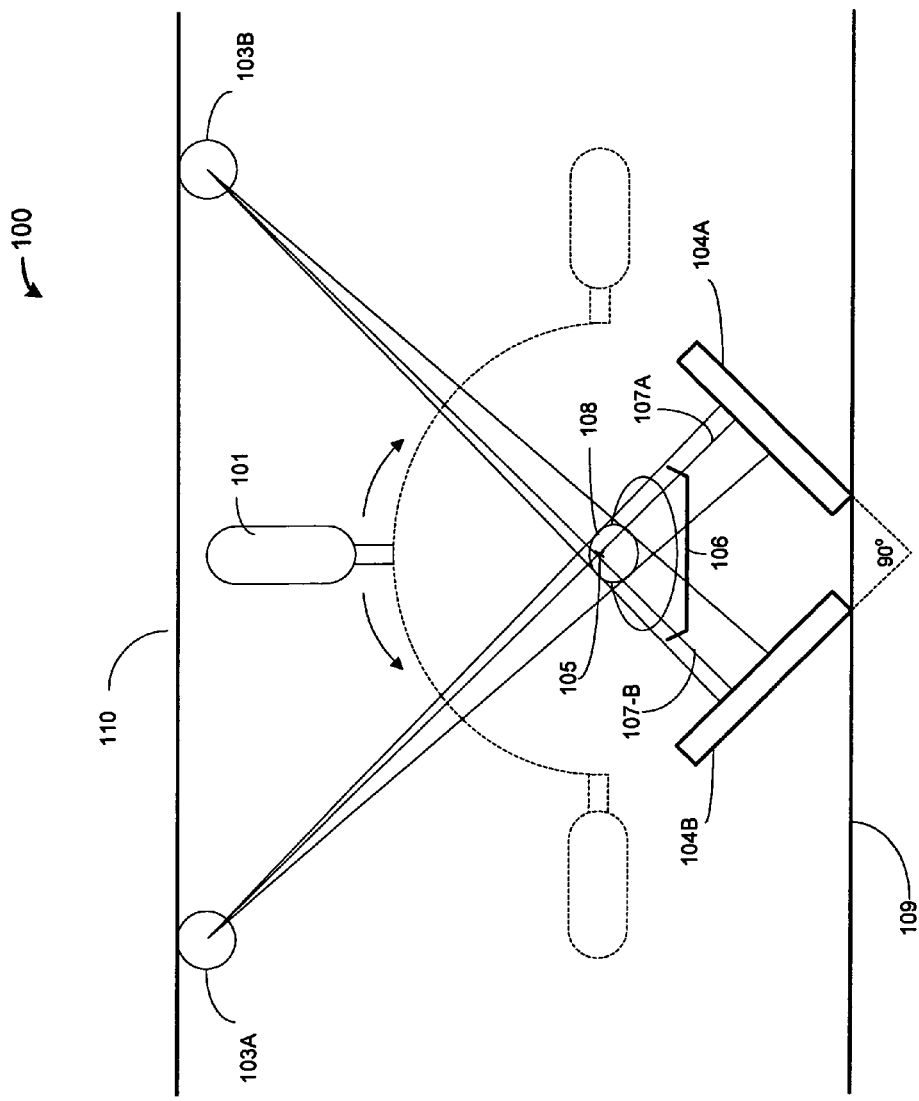
FIG. 2 illustrates the geometry of a conventional image-guided radiation treatment system.
Figure 3A:
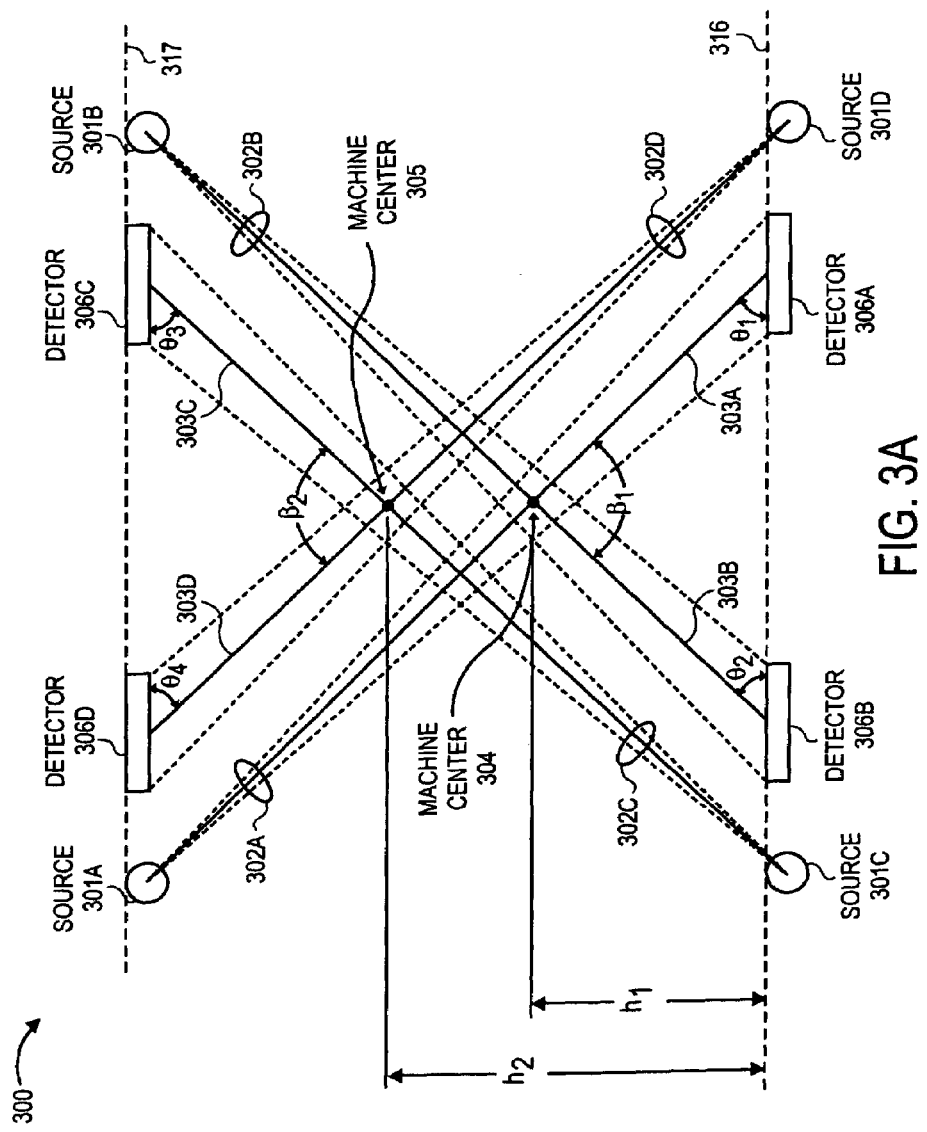
FIG. 3A illustrates an imaging system in one embodiment of imaging geometry.

FIG. 3A illustrates an imaging system 300 in one embodiment of an imaging geometry associated with a robotic-based IGRT system such as the CyberKnife® Radiosurgery System, manufactured by Accuray, Inc. of California. Imaging system 300 includes a first pair of x-ray sources 301A and 301B to generate a first x-ray beam 302A and a second x-ray beam 302B, where the axis 303A of the first x-ray beam and the axis 303B of the second x-ray beam define a first imaging plane. Imaging system 300 may also include a second pair of x-ray sources 301C and 301D to generate a third x-ray beam 302C and a fourth x-ray beam 302D, where the axis 303C of the third x-ray beam and the axis 303D of the fourth x-ray beam define a second imaging plane. The first x-ray beam 302A and the second x-ray beam 302B may be disposed to intersect at a first angle $\beta_1$ at a first imaging center 304. The third x-ray beam 302C and the fourth x-ray beam 302D may be disposed to intersect at a second angle $\beta_2$ at a second imaging center 305. Imaging system 300 may also include a first pair of x-ray detectors 306A and 306B in the first imaging plane to detect the first x-ray beam 302A and the second x-ray beam 302B, and a second pair of x-ray detectors 306C and 306D in the second imaging plane to detect the third x-ray beam 302C and the fourth x-ray beam 302D.

Thus, as illustrated in FIG. 3A, the imaging geometry of imaging system 300 may provide two imaging centers 304 and 305 located at different elevations. X-ray sources 301A and 301B may be located above the imaging centers and x-ray sources 301C and 301D may be located below the imaging centers. Angles $\beta_1$ and $\beta_2$ may be selected (e.g., by changing the separation between the x-ray sources and/or the x-ray detectors) to determine the location of the imaging centers with respect to one another and with respect to the x-ray sources and x-ray detectors. In particular, angles $\beta_1$ and $\beta_2$ may be selected to be equal angles (e.g., 90 degrees) such that the intersection of x-ray beam 302A and x-ray beam 302B is symmetrical with the intersection of x-ray beams 302C and 302D.

Figure 3B:
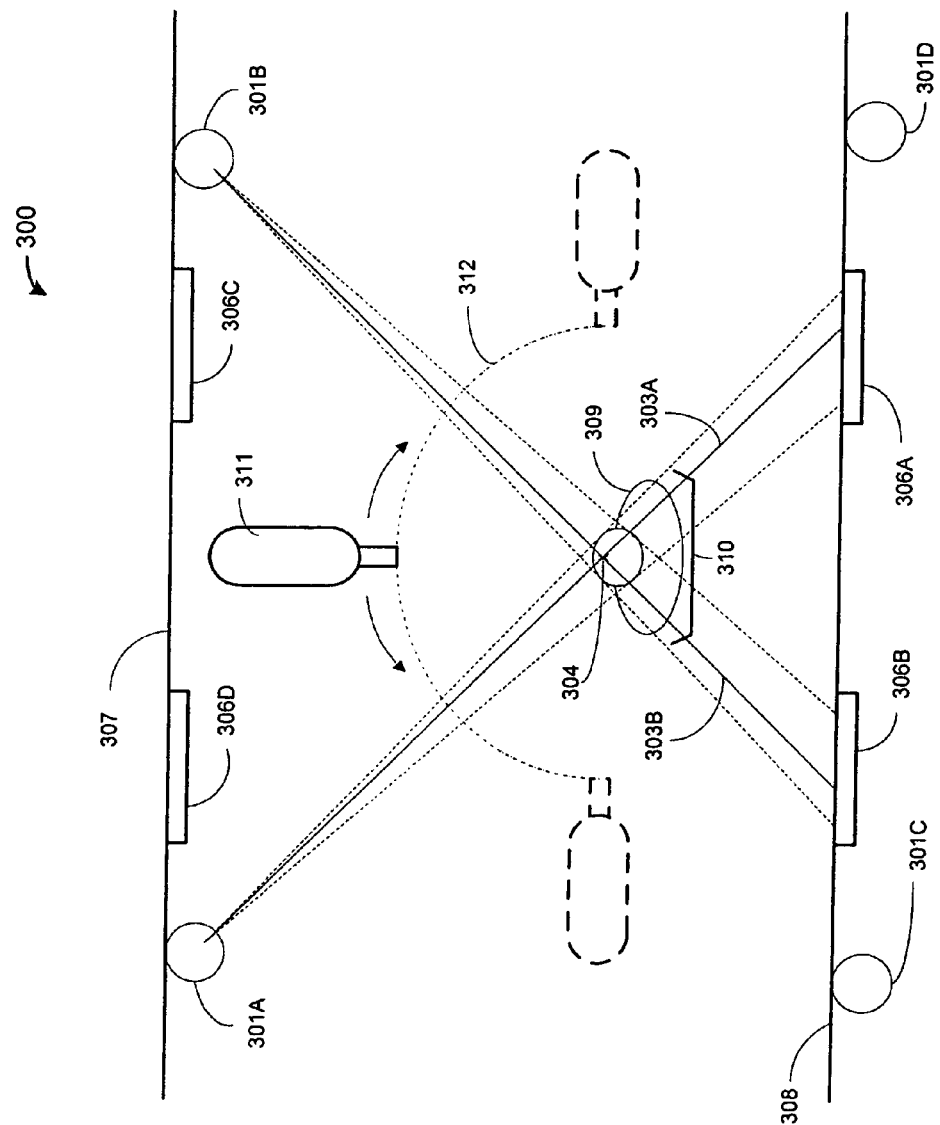
FIG. 3B illustrates one application of the embodiment of FIG. 3A.

Two imaging centers, such as imaging centers 304 and 305, may establish multiple treatment frames of reference and enable image-guided radiation treatment from above a patient and from below a patient. For example, as illustrated in FIG. 3B, x-ray sources 301A and 301B, and x-ray detectors 306C and 306D may be mounted on the ceiling 307 of an operating room. X-ray sources 301C and 301D, and x-ray detectors 306A and 306B may be mounted on the floor 308 of the operating room. If a patient 309 is positioned (e.g., by moving the patient on a robotic couch, such as treatment couch 310) near the first machine center 304, the patient may be imaged while a robotically controlled LINAC 311 administers radiation treatment from a region 312 above the patient. Region 312 may include a predefined set of treatment nodes or locations where LINAC 311 may be positioned to deliver radiation treatment from one or more angles. For example, region 312 may include 100 nodes and LINAC 311 may be positioned at 12 different angles at each node to deliver a total of 1200 individual treatment beams. In one embodiment, in the case of intracranial radiation treatment, for example, region 312 may be an approximately hemispherical region centered on the head of patient 309 with a radius from approximately 650 millimeters to approximately 800 millimeters. In an alternative embodiment, in the case of radiation treatment to the body of patient 309, region 312 may be an approximately cylindrical with a radius from approximately 900 mm to 1000 mm. Conversely, as illustrated in FIG. 3C, if the patient 309 is positioned near the second machine center 305, the patient may be imaged while the robotically controlled LINAC 311 administers radiation treatment from a region 313 below the patient which may mirror the same general dimensions as region 312.

Figure 4A:
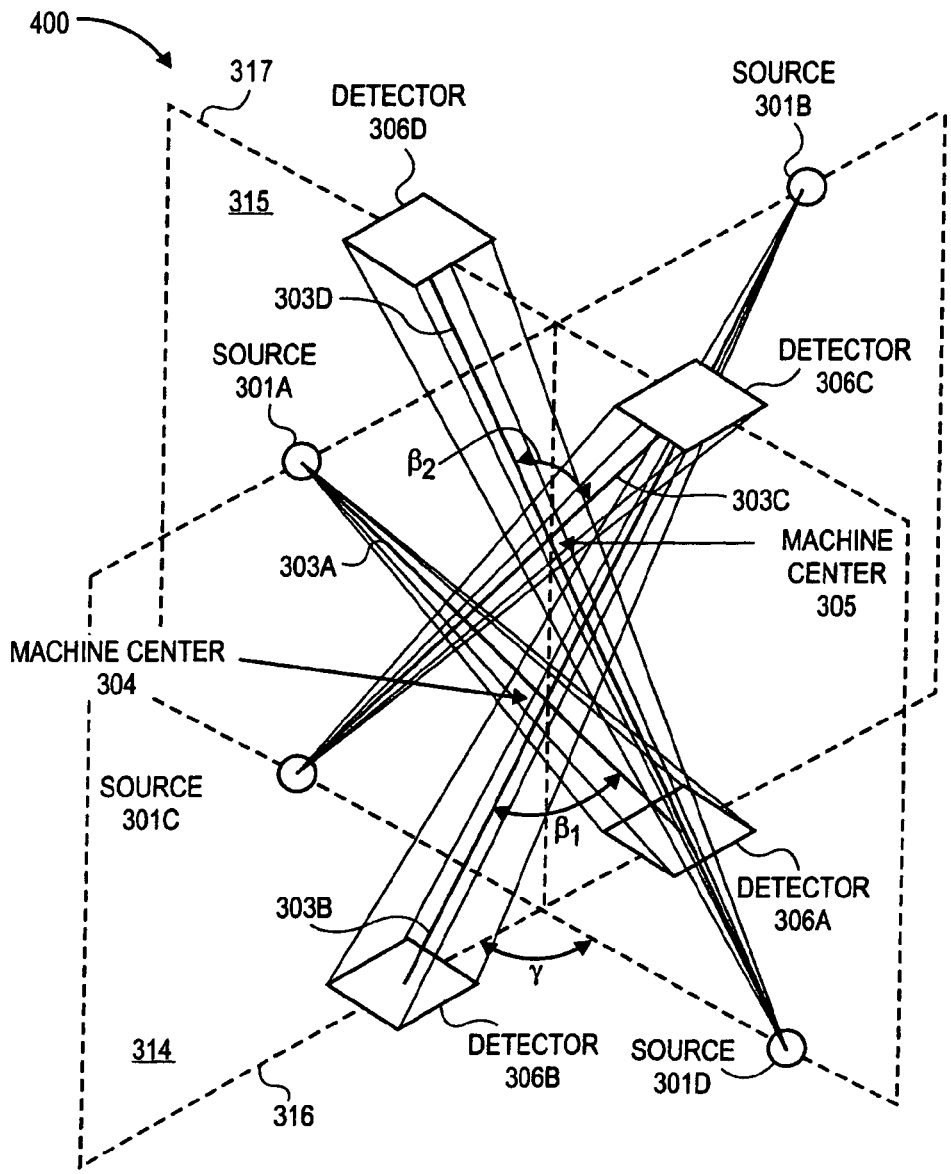
FIGS. 4A and 4B illustrate an imaging system in a second embodiment of imaging geometry.
Figure 4B:
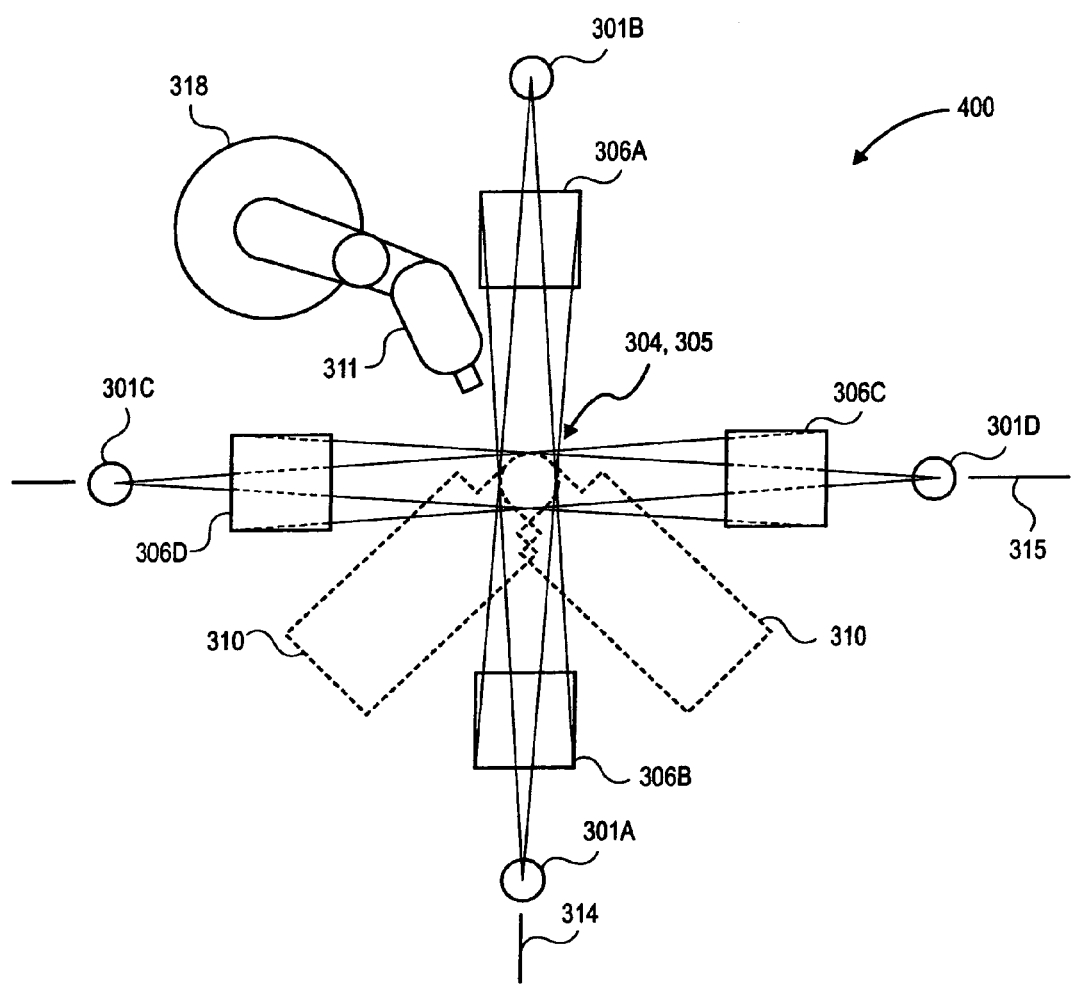

FIG. 3A illustrates an imaging system 300 where the first imaging plane and the second imaging plane are coplanar planes. Other configurations of the first imaging plane and the second imaging plane may be advantageous (e.g., to best utilize limited floor space in an operating room or to reduce the number of blocked treatment nodes). FIG. 4A illustrates an alternative embodiment of a system 400 where the first imaging plane 314 is rotated at an angle γ with respect to the second imaging plane 315. In one embodiment, as illustrated in FIG. 4B as a top down view of system 400, γ may be a ninety degree angle. FIG. 4B illustrates how treatment couch 310 may be positioned at multiple angles with respect to LINAC 311 on robotic arm 320, with respect to image planes 314 and 315, and also with respect to machine centers 304 and 305. It will be appreciated that the positioning flexibility provided by the configuration of system 400 may eliminate the problem of blocked treatment nodes described above.

Returning now to FIG. 3A, it will be observed that x-ray detector 306A may be disposed at an imaging angle $\theta_1$ with respect to the axis 303A of x-ray beam 302A. Likewise, x-ray detectors 306B, 306C and 306D may be disposed at imaging angles $\theta_2$, $\theta_3$ and $\theta_4$ with respect to the axes 303B, 303C and 303D of x-ray beams 302B, 302C and 302D. In one embodiment, imaging angles $\theta_1$ through $\theta_4$ may be ninety degree angles, such that the imaging surfaces of x-ray detectors 306A through 306D are all perpendicular to the axes of their respective x-ray beams. In another embodiment, imaging angles $\theta_1$ through $\theta_4$ may be acute angles selected to dispose x-ray detectors 306A and 306B along a baseline 316 in the first imaging plane 314, and to dispose x-ray detectors 306C and 306D along a topline 317 in the second imaging plane 315. In one embodiment, baseline 316 and topline 317 may correspond to the ceiling 307 and the floor 308 of FIGS. 3B and 3C.

Figure 5:
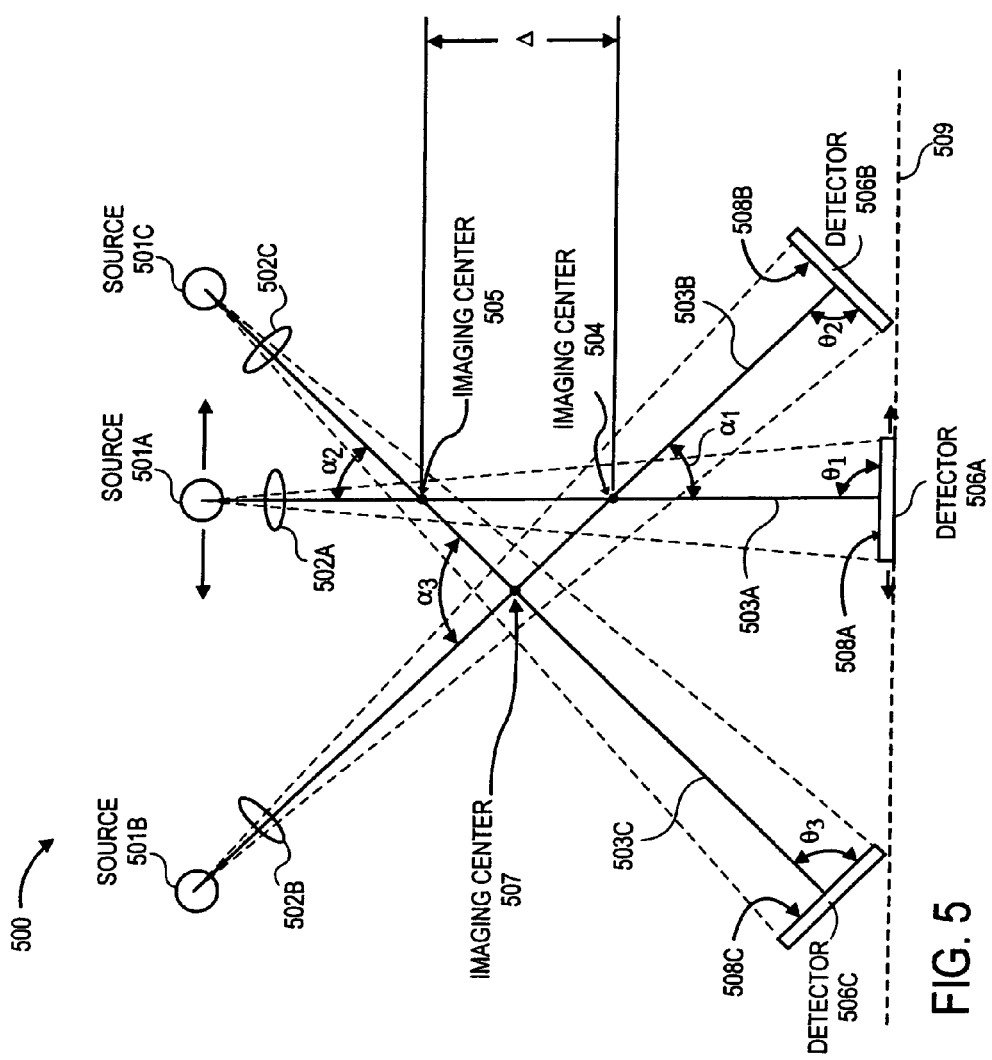
FIG. 5 illustrates an imaging system in a third embodiment of imaging geometry.

In one embodiment of imaging geometry, as illustrated in FIG. 5, an imaging system 500 may include three x-ray sources and three x-ray detectors. In FIG. 5, a first x-ray source 501A may project an x-ray beam 502A, having an axis 503A, onto an imaging surface 508A of a first x-ray detector 506A. A second x-ray source 501B may project an x-ray beam 502B, having an axis 503B, onto an imaging surface 508B of a second x-ray detector 506B. X-ray beam 502B may be disposed to intersect x-ray beam 502A such that axis 503B intersects axis 503A at a first imaging center 504 at an angle $\alpha_1$. A third x-ray source 501C may project a third x-ray beam, having an axis 503C, onto an imaging surface 508C of a third x-ray detector 506C. X-ray beam 502C may be disposed to intersect x-ray beam 502A such that axis 503C intersects axis 503A at a second imaging center 505 at a second angle $\alpha_2$. X-ray beam 502C may also be disposed to intersect x-ray beam 502B such that axis 503C intersects axis 503B at a third imaging center 507 at an angle $\alpha_3$.

In one embodiment, imaging surface 508A may be disposed at an imaging angle $\phi_1$ with respect to axis 503A, imaging surface 508B may be disposed at an imaging angle $\phi_2$ with respect to axis 503B, and imaging surface 508C may be disposed at an imaging angle $\phi_3$ with respect to axis 503C. In one embodiment, angles $\phi_1$, $\phi_2$ and $\phi_3$ may be right angles. In other embodiments, one or more of angles $\phi_1$, $\phi_2$, and $\phi_3$ may be selected such that imaging surfaces 508A, 508B and 508C are parallel to a baseline 509.

In one embodiment, x-ray source 501A and x-ray detector 506A may each be configured to move horizontally, together or independently, in order to adjust the points of intersection of the first x-ray beam 502A with the second x-ray beam 502B and the third x-ray beam 502C, in order to adjust the locations of the first imaging center 504 and the second imaging center 505, and/or the separation A between the first imaging center 504 and the second imaging center 505.

Figure 6:
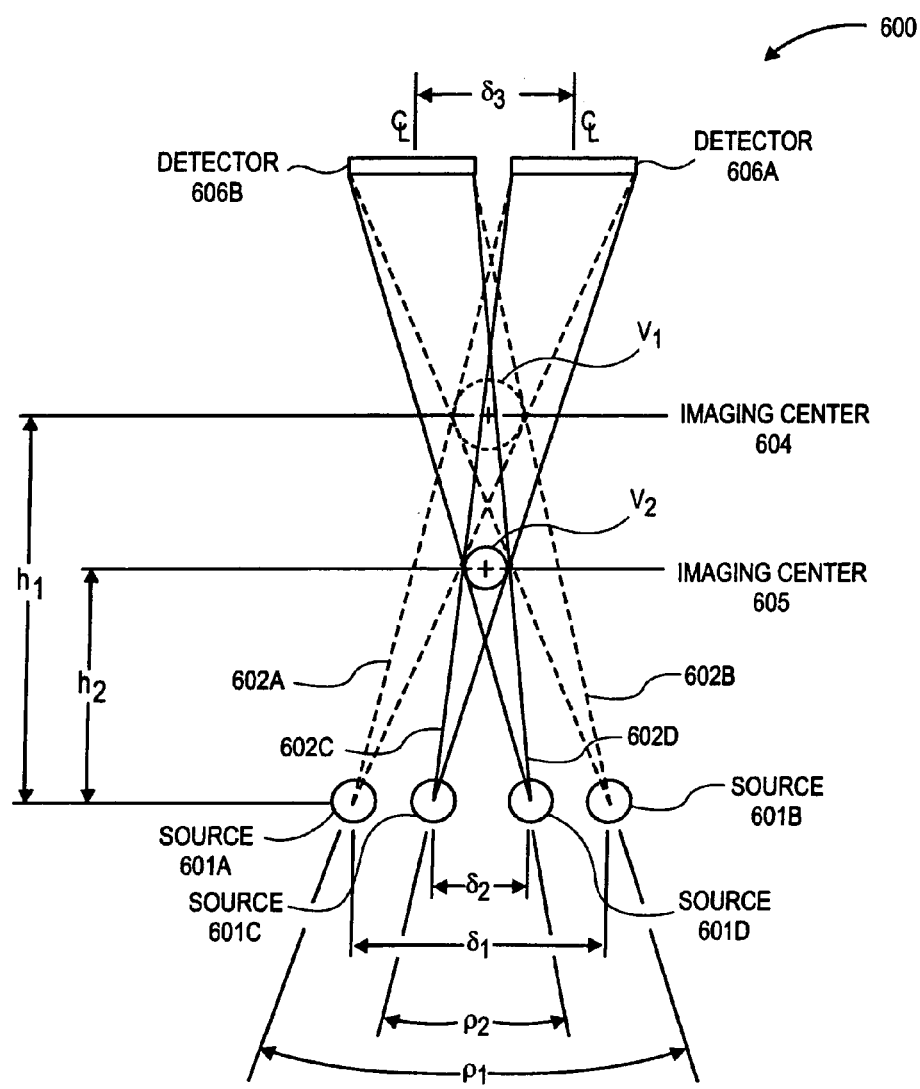
FIG. 6 illustrates an imaging system in a fourth embodiment of imaging geometry.

FIG. 6 illustrates an imaging system 600 in yet another embodiment of imaging geometry. Imaging system 600 includes a first pair of x-ray sources 601A and 601B at a separation $\delta_1$ to project a first x-ray beam 602A and a second x-ray beam 602B to intersect at an angle $\rho_1$ at a first imaging center 604, located at a height $h_1$ above the x-ray sources. Imaging system 600 may also include a second pair of x-ray sources 601C and 601D at a separation $\delta_2$ to project a third x-ray beam 602C and a fourth x-ray beam 602D to intersect at an angle $\rho_2$ at a second imaging center 605, located at a height $h_2$ above the x-ray sources. Separations $\delta_1$, $\delta_2$ and $\delta_3$ may be selected to adjust the angles $\rho_1$ and $\rho_2$, and the locations of imaging centers 604 and 605. As illustrated in FIG. 6, imaging center 604 is enclosed by an imaging volume $V_1$, subtended by x-ray beams 602A and 602B. Imaging center 605 is enclosed by an imaging volume $V_2$, subtended by x-ray beams 602C and 602D. Volumes V1 and V2 may also be adjusted by selecting separations $\delta_1$, $\delta_2$, and $\delta_3$. Although not illustrated, it will be appreciated that the geometry of FIG. 6 may be inverted. That is, the locations of the x-ray sources and x-ray detectors may be reversed.

Figure 7:
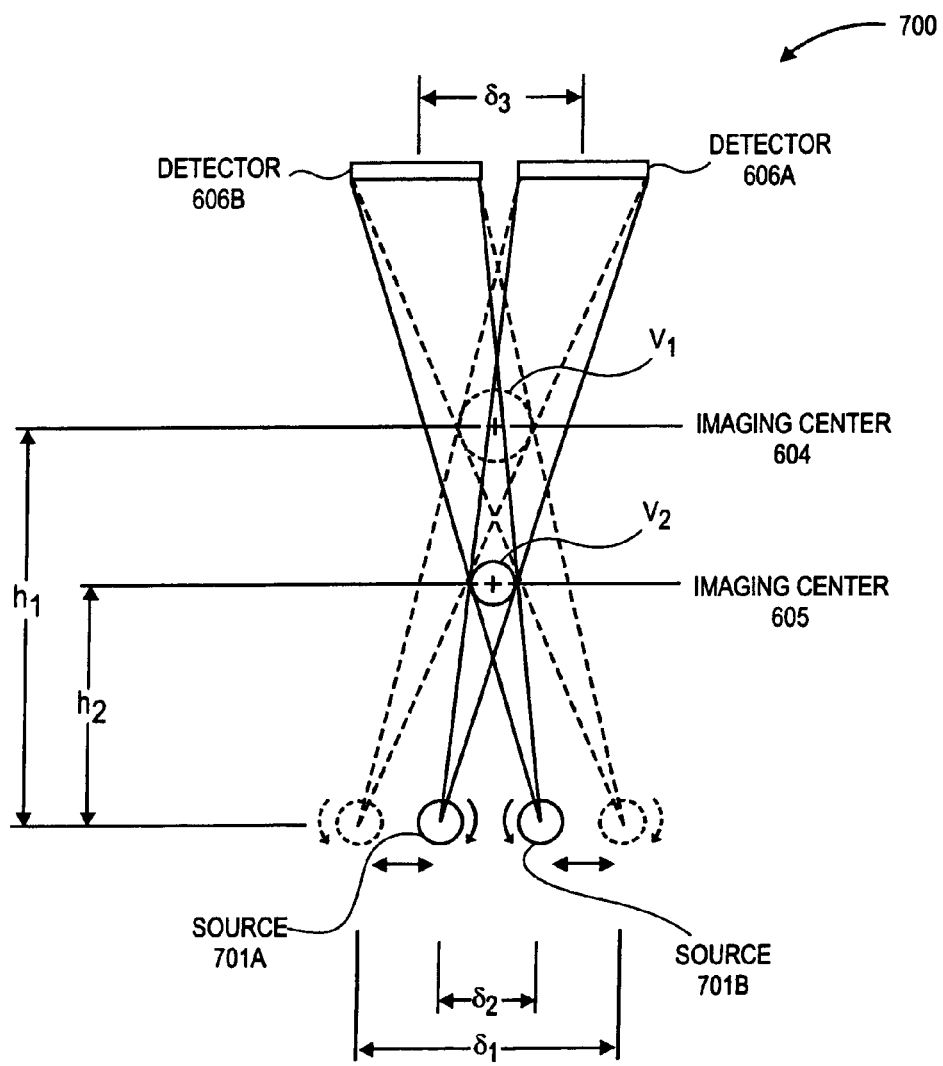
FIG. 7 illustrates an imaging system in a fifth embodiment of imaging geometry.

FIG. 7 illustrates a system 700 in another embodiment of imaging geometry. System 700 includes a single pair of movable x-ray sources which may be configured to maintain alignment with x-ray detectors 606A and 606B when x-ray sources 701A and 701B are at either separation $\delta_1$ or $\delta_2$. Methods for maintaining angular alignments through linear displacements are known in the art and will not be described, herein. Thus, it will be appreciated that imaging system 700 may provide the same functionality as imaging system 600 with only two x-ray sources.

Figure 8A:
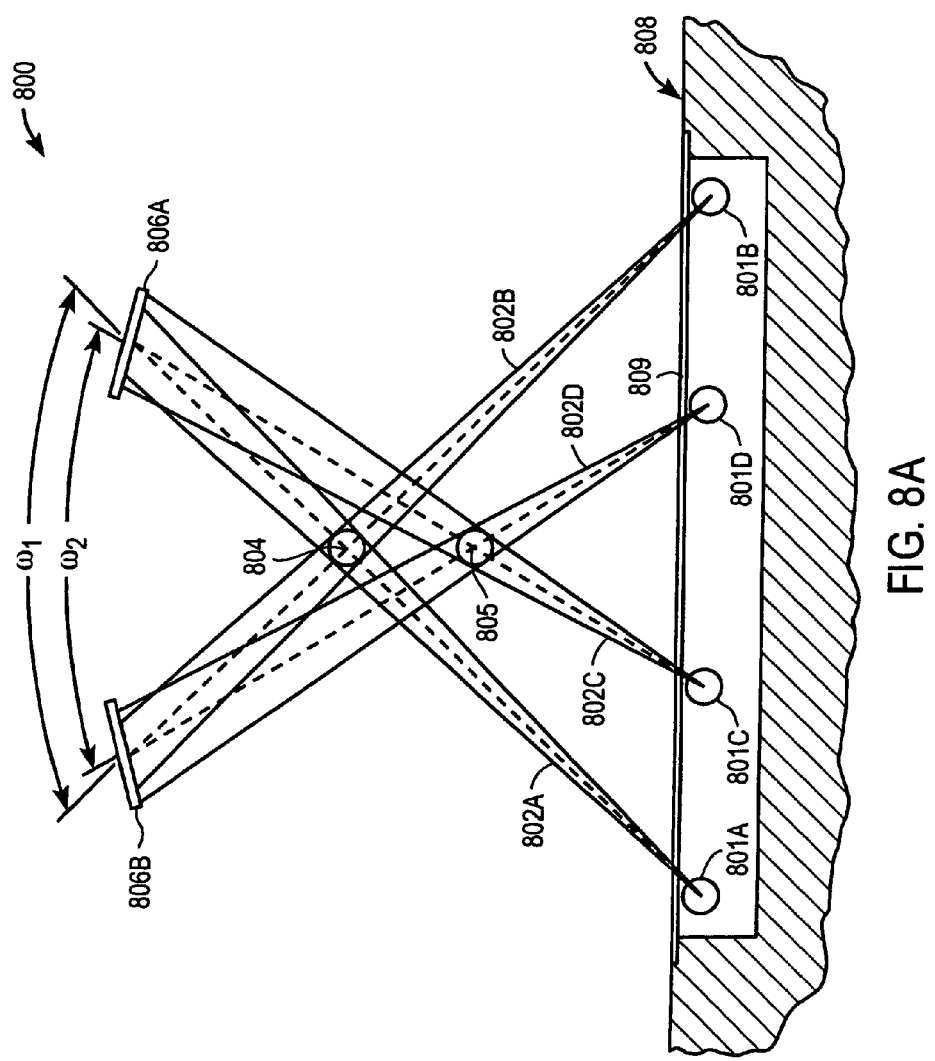
FIG. 8A illustrates an imaging system in a sixth embodiment of imaging geometry.

FIG. 8A illustrates an imaging system 800 in another embodiment of imaging geometry. Imaging system 800 includes two pairs of x-ray sources 801A and 801B, and 801C and 801D mounted below a floorline 808 and covered by an x-ray transparent material 809. It will be appreciated that mounting the x-ray sources below the floorline may maximize the space available within an operating theater to position a LINAC, such as LINAC 311 for treatment. X-ray sources 801A and 801B may project x-ray beams 802A and 802B that intersect at imaging center 804 and illuminate x-ray detectors 806A and 806B, respectively. X-ray sources 801C and 801D may project x-ray beams 802C and 802D that intersect at imaging center 805 and illuminate x-ray detectors 806A and 806B, respectively.

Figure 8B:
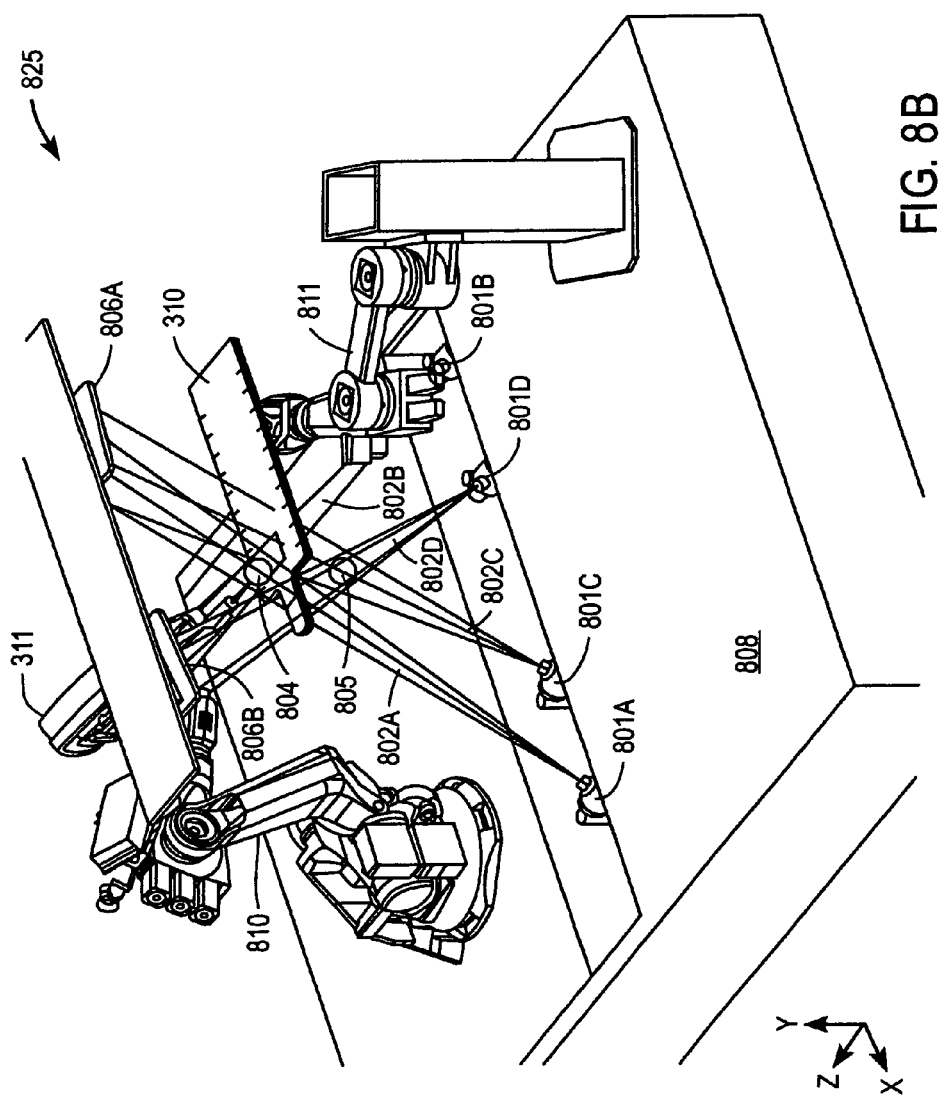
FIGS. 8B and 8C illustrate a treatment delivery system incorporating the embodiment of FIG. 8A.
Figure 8C:
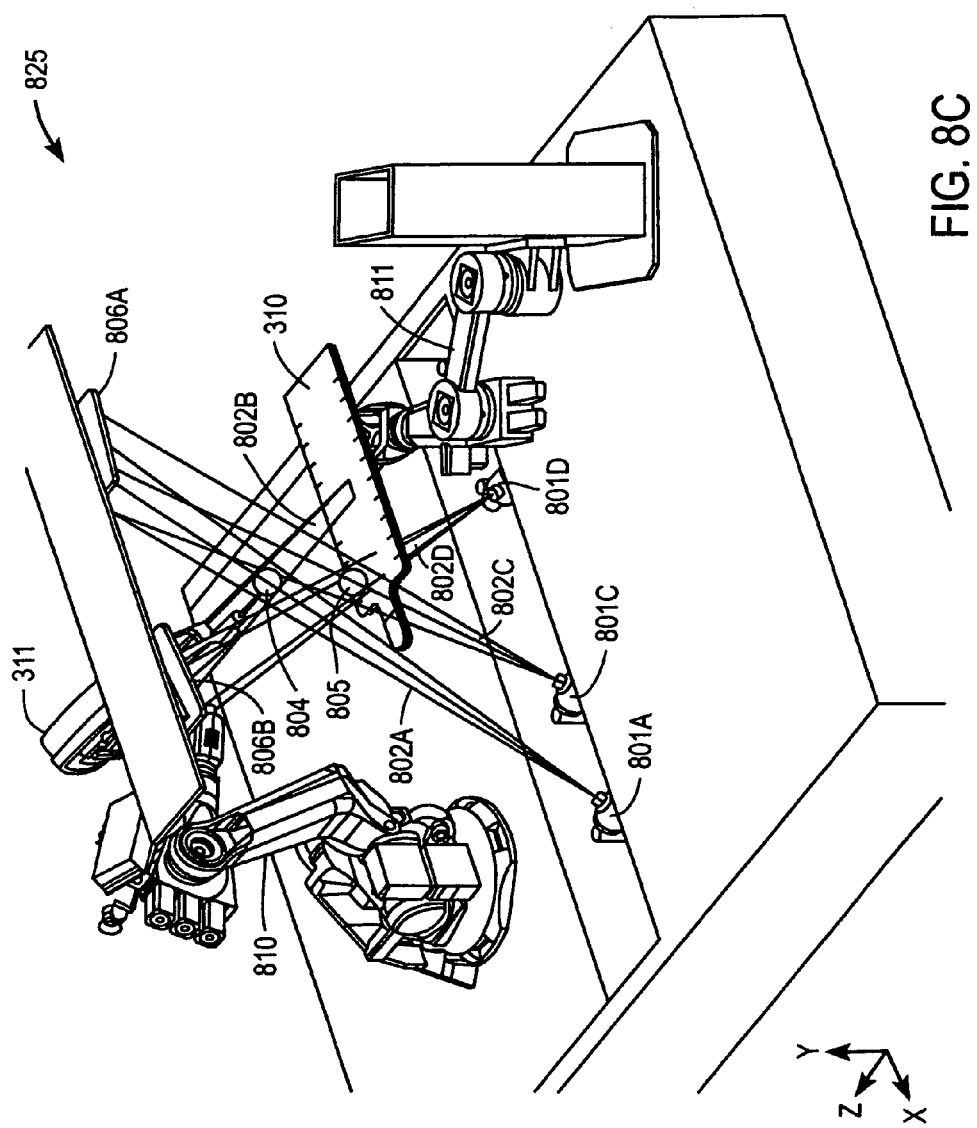

FIGS. 8B and 8C illustrate an example of a radiation treatment delivery system 825 incorporating the imaging system of FIG. 8A. Radiation treatment delivery system 825 includes a LINAC 311 mounted on a robotic arm 810. The system also includes a robotic arm assembly 811, with multiple degrees of freedom of motion (e.g., five or more) to position treatment couch 310 at multiple positions relative to imaging centers 804 and 805. FIG. 8B illustrates treatment couch 310 positioned in proximity to imaging center 804, and FIG. 8C illustrates treatment couch 310 positioned in proximity to imaging center 805.

Figure 9B:
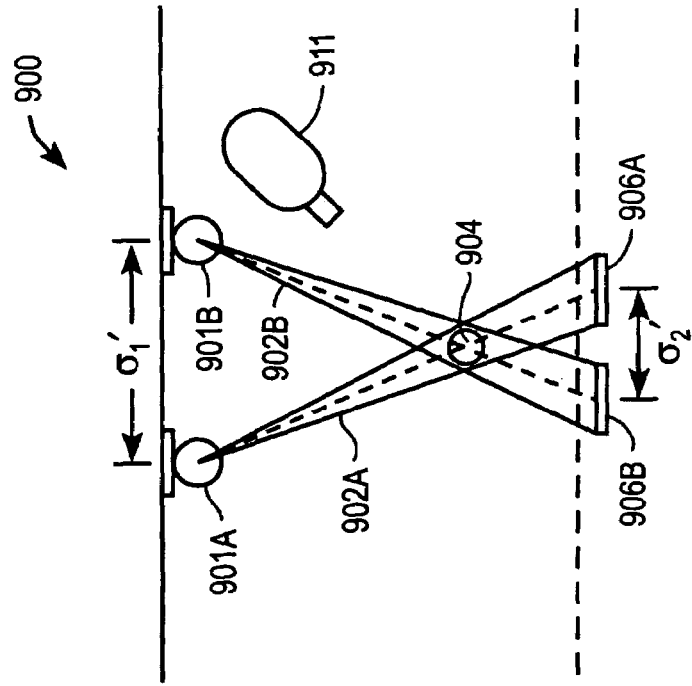
FIGS. 9A and 9B illustrate an imaging system in a seventh embodiment of imaging geometry.
Figure 9A:
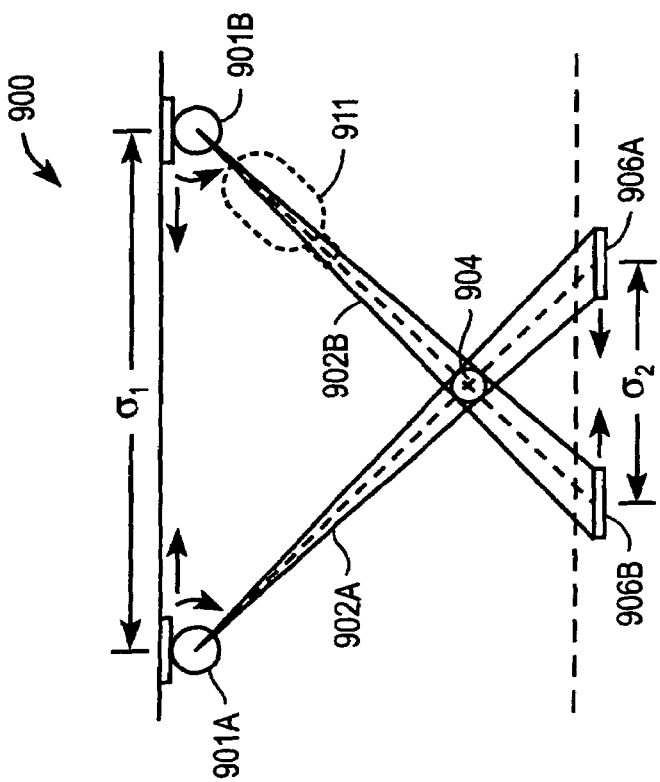

FIGS. 9A and 9B illustrate an imaging system 900 in a further embodiment of imaging geometry. Imaging system 900 includes a pair of movable x-ray sources 901A and 901B which may be linearly translated to change the separation between the x-ray sources from $\sigma_1$ to $\sigma_1'$. Imaging system 900 may also include a pair of movable x-ray detectors 906A and 906B which may be linearly translated to change the separation between the x-ray detectors from $\sigma_2$ to $\sigma_2'$. In FIG. 9A, x-ray beams 902A and 902B intersect at image center 904. At the position of the x-ray sources and x-ray detectors illustrated in FIG. 9a, it can be seen that treatment cannot be provided by LINAC 911 (shown in dotted line) because positioning the LINAC as shown will block x-ray beam 902B and prevent imaging system 900 from obtaining a stereoscopic image. FIG. 9B illustrates imaging system 900 with x-ray sources 901A and 901B, and x-ray detectors 906A and 906B, repositioned to generate x-ray beams that intersect at imaging center 904 without being blocked by LINAC 911.

Figure 10:
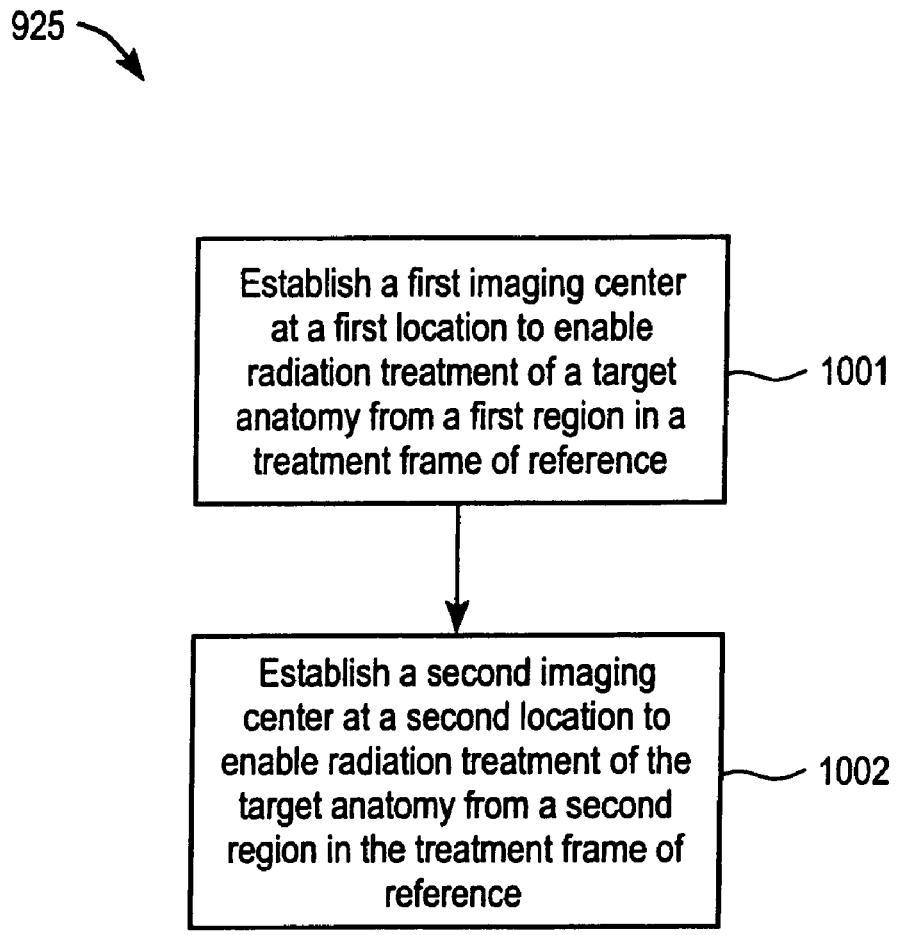
FIG. 10 is a flowchart illustrating a method in one embodiment of imaging geometry.

FIG. 10 is a flowchart illustrating a method 925 in one embodiment of an imaging geometry. With reference to FIGS. 3A-3C and 4A, the method includes establishing a first imaging center 304 at a first location h1 to enable radiation treatment of a target anatomy 309 from a first region 312 in a treatment frame of reference (step 1001). The method also includes establishing a second imaging center 305 at a second location h2 to enable radiation treatment of the target anatomy 309 from a second region 313 in the treatment frame of reference (step 1002).

In one embodiment, establishing the first imaging center (step 1001) may include generating a first imaging beam 302A having a first axis 303A, and a second imaging beam 302B having a second axis 303B, the first axis and the second axis defining a first image plane 314, the second imaging beam disposed at a first angle $\beta_1$ with respect to the first imaging beam to intersect the first imaging beam at the first location. In one embodiment, establishing the second imaging center (step 1002) may include generating a third imaging beam 302C having a third axis 303C, and a fourth imaging beam 302D having a fourth axis 303, the third axis and the fourth axis defining a second image plane 315, the fourth imaging beam disposed at a second angle $\beta_2$ with respect to the third imaging beam to intersect the third imaging beam at the first location.

Figure 11:
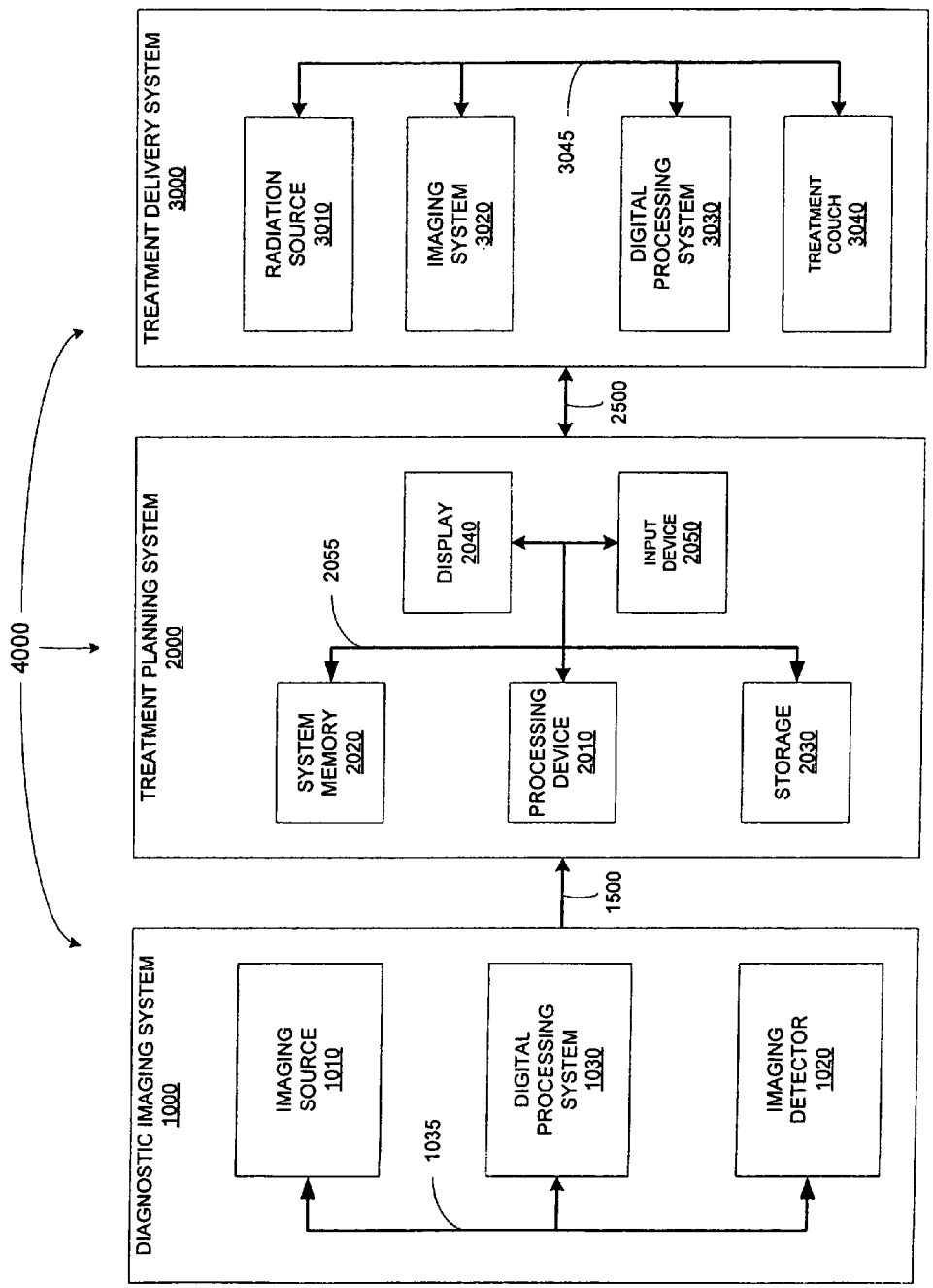
FIG. 11 illustrates a system in which embodiments of imaging geometry may be practiced.

FIG. 11 illustrates one embodiment of systems that may be used in performing radiation treatment in which features of the present invention may be implemented. As described below and illustrated in FIG. 10, system 4000 may include a diagnostic imaging system 1000, a treatment planning system 2000 and a treatment delivery system 3000.

Diagnostic imaging system 1000 may be any system capable of producing medical diagnostic images of a volume of interest (VOI) in a patient that may be used for subsequent medical diagnosis, treatment planning and/or treatment delivery. For example, diagnostic imaging system 1000 may be a computed tomography (CT) system, a magnetic resonance imaging (MRI) system, a positron emission tomography (PET) system, a single photon emission CT (SPECT), an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 1010 and the imaging detector 1020 are coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing treatment planning operations discussed herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM)

and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 includes a therapeutic and/or surgical radiation source 3010 (e.g., LINAC 311) to administer a prescribed radiation dose to a target volume in conformance with a treatment plan. Treatment delivery system 3000 may also include an imaging system 3020 to capture intra-treatment images of a patient volume (including the target volume) for registration or correlation with the diagnostic images described above in order to position the patient with respect to the radiation source. Imaging system 3020 may include any of the imaging systems and imaging geometries described above (e.g., systems 300, 400, 500, 600, 700, 800 and 900). Treatment delivery system 3000 may also include a digital processing system 3030 to control radiation source 3010, imaging system 3020 and a patient support device such as a treatment couch 3040. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may implement algorithms to register images obtained from imaging system 3020 with pre-operative treatment planning images in order to align the patient on the treatment couch 3040 within the treatment delivery system 3000, and to precisely position the radiation source with respect to the target volume.

The treatment couch 3040 may be coupled to a robotic arm (not shown) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the Axum® treatment couch developed by Accuray, Inc. of California, or be another type of conventional treatment table known to those of ordinary skill in the art.

Figure 12:
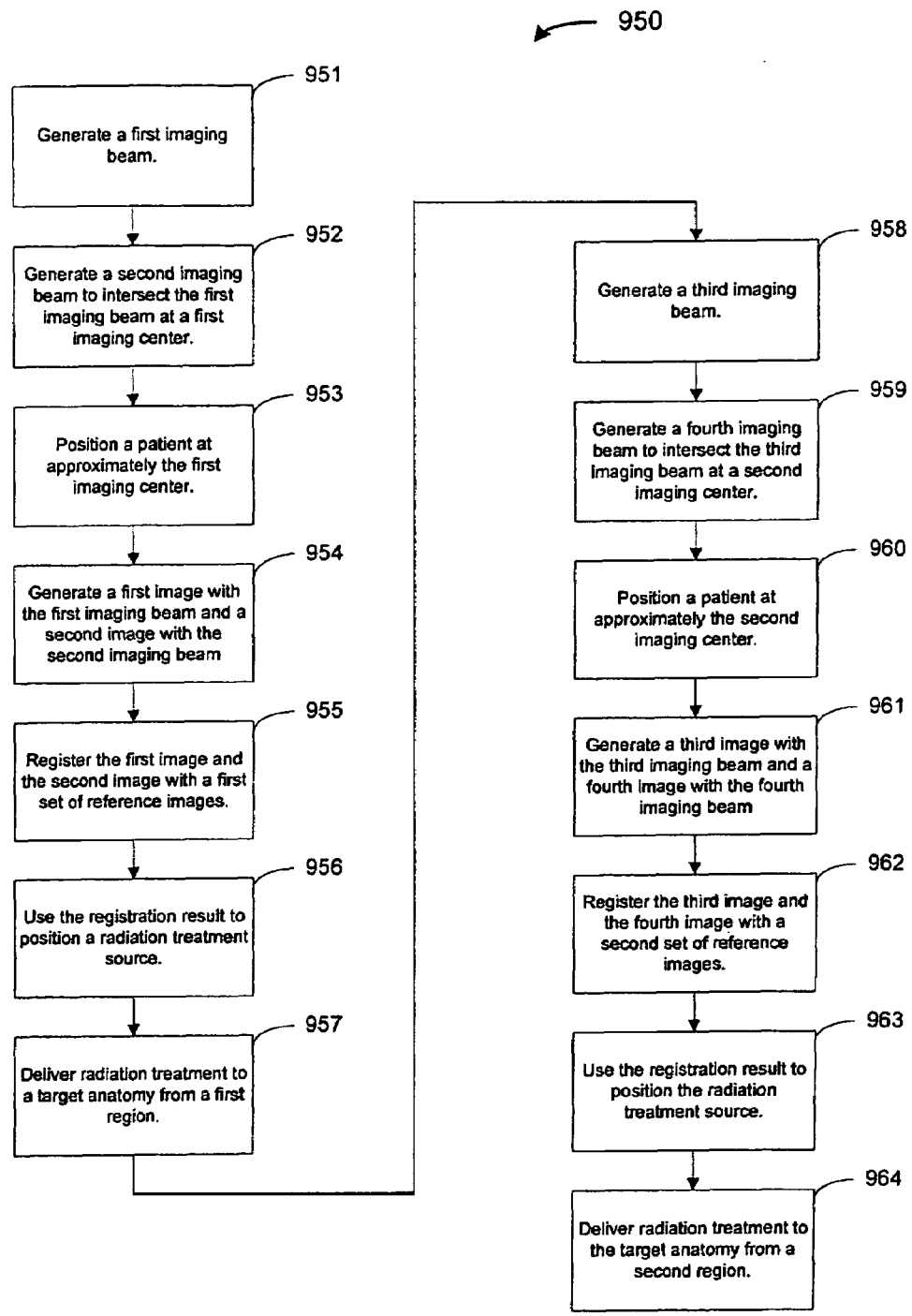
FIG. 12 is a flowchart illustrating a method in one embodiment of imaging geometry.

FIG. 12 is a flowchart illustrating a method 950 in one embodiment of imaging geometry. With reference, again, to FIGS. 3B and 3C, the method begins at step 951 by generating a first imaging beam 302A. At step 952, a second imaging beam 302B is generated to intersect the first imaging beam at a first imaging center 304. At step 953, a patient 309 is positioned at approximately the first imaging center. At step 954, a first image is generated with the first imaging beam and a second image is generated with the second imaging beam. At step 955, the first image and the second image are registered with a first set of pre-treatment reference images. At step 956, the registration result is used to position a radiation treatment source (e.g., the LINAC 311). At step 957, radiation treatment is delivered to a target anatomy in the patient 309 from a first range of angles 312. At step 958, a third imaging beam 303C is generated. At step 959, a fourth imaging beam 302D is generated to intersect the third imaging beam at a second imaging center 305. At step 960, the patient 309 is positioned at approximately the second imaging center. At step 961, a third image is generated with the third imaging beam and a fourth image is generated with the fourth imaging beam. At step 962, the third image and the fourth image are registered with a second set of pre-treatment reference images. At step 963, the registration result is used to position the radiation treatment source (e.g., the LINAC 311). At step 964, radiation treatment is delivered to the target anatomy in the patient 309 from a second range of angles 313.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

While some specific embodiments of the invention have been shown the invention is not to be limited to these embodiments. The invention is to be understood as not limited by the specific embodiments described herein, but only by scope of the appended claims.

We claim:

1. A method for stereoscopic imaging in a radiation treatment system, comprising:
   establishing a first imaging center by generating a first pair of imaging beams at a first location to enable radiation treatment of a target anatomy from a first region in a treatment frame of reference;
   establishing a second imaging center by generating a second pair of imaging beams at a second location to enable radiation treatment of the target anatomy from a second region in the treatment frame of reference, wherein the first location and the second location are different locations; and, generating control signals representative of the first and the second imaging centers.

2. The method of claim 1, wherein establishing the first imaging center comprises generating a first imaging beam having a first axis and a second imaging beam having a second axis, the first axis and the second axis defining a first imaging plane, the second imaging beam disposed at a first angle with respect to the first imaging beam to intersect the first imaging beam at the first location.

3. The method of claim 2, wherein establishing the second imaging center comprises generating a third imaging beam having a third axis in the first imaging plane, the third imaging beam disposed at a second angle with respect with respect to the first imaging beam to intersect the first imaging beam at the second location.

4. The method of claim 3, wherein the third imaging beam is disposed at a third angle with respect to the second imaging beam, further comprising establishing a third imaging center at a third location comprising an intersection of the second imaging beam and the third imaging beam in the first imaging plane.

5. The method of claim 2, wherein establishing the second imaging center comprises generating a third imaging beam having a third axis and a fourth imaging beam having a fourth axis, the third axis and the fourth axis defining a second imaging plane, the fourth imaging beam disposed at a second angle with respect to the third imaging beam to intersect the third imaging beam at the second location.

6. The method of claim 5, wherein the first imaging plane and the second imaging plane are coplanar planes.

7. The method of claim 5, wherein the first imaging plane and the second imaging plane are non-coplanar planes.

8. The method of claim 3, further comprising:
   positioning the target anatomy at approximately the first imaging center;
   generating a first image with the first imaging beam and a second image with the second imaging beam;
   registering the first image and the second image with a first plurality of reference images to obtain a first registration result;
   positioning a radiation treatment source with the first registration result; and
   delivering radiation treatment to the target anatomy from a first range of angles.

9. The method of claim 8, further comprising:
   positioning the target anatomy at approximately the second imaging center;
   generating a third image with the third imaging beam and a fourth image with the first imaging beam;
   registering the third image and the fourth image with a second plurality of reference images to obtain a second registration result;
   positioning the radiation treatment source with the second registration result; and
   delivering radiation treatment to the target anatomy from a second range of angles.

10. The method of claim 4, further comprising:
    positioning the target anatomy at approximately the third imaging center;
    generating a first image with the second imaging beam and a second image with the third imaging beam;
    registering the first image and the second image with a plurality of reference images to obtain a registration result;
    positioning a radiation treatment source with the registration result; and
    delivering radiation treatment to the target anatomy from a third range of angles.

11. The method of claim 5, further comprising:
    positioning the target anatomy at approximately the first imaging center;
    generating a first image with the first imaging beam and a second image with the second imaging beam;
    registering the first image and the second image with a first plurality of reference images to obtain a first registration result;
    positioning a radiation treatment source with the first registration result; and
    delivering radiation treatment to the target anatomy from the first range of angles.

12. The method of claim 11, further comprising:
    positioning the target anatomy at approximately the second imaging center;
    generating a third image with the third imaging beam and a fourth image with the fourth imaging beam;
    registering the third image and the fourth image with a second plurality of reference images to obtain a second registration result;
    positioning the radiation treatment source with the second registration result; and
    delivering radiation treatment to the target anatomy from the second range of angles.

13. An imaging system, comprising:
    a first pair of x-ray sources to generate a first x-ray beam having a first axis and a second x-ray beam having a second axis, the first axis and the second axis defining a first imaging plane, the first x-ray beam and the second x-ray beam disposed to intersect at a first angle at a first imaging center;
    a second pair of x-ray sources to generate a third x-ray beam having a third axis and a fourth x-ray beam having a fourth axis, the third axis and the fourth axis defining a second imaging plane, the third x-ray beam and the fourth x-ray beam disposed to intersect at a second angle at a second imaging center, wherein the first imaging center and the second imaging center are different imaging centers;
    a first pair of x-ray detectors in the first imaging plane to detect the first x-ray beam and the second x-ray beam; and a second pair of x-ray detectors in the second imaging plane to detect the third x-ray beam and the fourth x-ray beam.

14. The imaging system of claim 13, wherein the first pair of x-ray sources is located above the first imaging center and the second imaging center, wherein the second pair of x-ray sources is located below the first imaging center and the second imaging center, and wherein the second imaging center is located above the first imaging center.

15. The imaging system of claim 14, wherein the first angle is equal to the second angle.

16. The imaging system of claim 15, wherein the first angle and the second angle are ninety degree angles.

17. The imaging system of claim 14, wherein the first imaging plane and the second imaging plane are coplanar planes.

18. The imaging system of claim 14, wherein the first imaging plane is rotated at an angle from the second imaging plane.

19. The imaging system of claim 14, wherein the first imaging plane and the second imaging plane are orthogonal planes.

20. The imaging system of claim 13, wherein
the first pair of x-ray detectors comprises a first x-ray detector having a first imaging surface disposed at a first imaging angle to the first axis, and a second x-ray detector having a second imaging surface disposed at a second imaging angle to the second axis, and wherein
the second pair of x-ray detectors comprises a third x-ray detector having a third imaging surface disposed at a third imaging angle to the third axis, and a fourth x-ray detector having a fourth imaging surface disposed at a fourth imaging angle to the fourth axis.

21. The imaging system of claim 20, wherein each of the first imaging angle, the second imaging angle, the third imaging angle and the fourth imaging angle is a right angle.

22. The imaging system of claim 17, wherein each of the first imaging angle, the second imaging angle, the third imaging angle and the fourth imaging angle is an acute angle.

23. An imaging system, comprising:
a first x-ray source to generate a first x-ray beam having a first axis, and a first x-ray detector having an imaging surface to detect the first x-ray beam;
a second x-ray source to generate a second x-ray beam having a second axis, and a second x-ray detector having a second imaging surface to detect the second x-ray beam, the first axis and the second axis defining an imaging plane, the first x-ray beam and the second x-ray beam disposed to intersect at a first angle at a first imaging center in the imaging plane; and
a third x-ray source to generate a third x-ray beam having a third axis, and a third x-ray detector having a third imaging surface to detect the third x-ray beam, the third x-ray beam disposed to intersect the first x-ray beam at a second angle at a second imaging center in the imaging plane, wherein the first imaging center and the second imaging center are different imaging centers, and to intersect the second x-ray beam at a third angle at a third imaging center in the imaging plane.

24. The imaging system of claim 23, wherein the first imaging surface is disposed at a first imaging angle to the first axis, the second imaging surface is disposed at a second imaging angle to the second axis, and the third imaging surface is disposed at a third imaging angle to the third axis.

25. The imaging system of claim 24, wherein each of the first imaging angle, the second imaging angle and the third imaging angle is a right angle.

26. The imaging system of claim 24, wherein one or more of the first imaging angle, the second imaging angle and the third imaging angle is selected to align the first imaging surface, the second imaging surface and the third imaging surface in a horizontal plane.

27. The imaging system of claim 24, wherein the first x-ray source is a movable x-ray source and the first x-ray detector is a movable x-ray detector, the first x-ray source and the first x-ray detector comprising a movable source-detector pair to adjust the locations of the first imaging center and the second imaging center in the imaging plane.

28. An imaging system, comprising:
a first pair of x-ray sources at a first separation to generate a first x-ray beam and a second x-ray beam in an imaging plane, the first x-ray beam and the second x-ray beam disposed to intersect at a first angle at a first imaging center;
a second pair of x-ray sources at a second separation to generate a third x-ray beam and a fourth x-ray beam in the imaging plane, the third x-ray beam and the fourth x-ray beam disposed to intersect at a second angle at a second imaging center, wherein the first imaging center and the second imaging center are different imaging centers; and
a pair of x-ray detectors at a third separation, comprising a first x-ray detector and a second x-ray detector, the first x-ray detector to detect the first x-ray beam and the third x-ray beam, the second x-ray detector to detect the second x-ray beam and the fourth x-ray beam.

29. The imaging system of claim 28, wherein the first pair of x-ray sources and the second pair of x-ray sources are located above the first imaging center and the second imaging center, and wherein the pair of x-ray detectors is located below the first imaging center and the second imaging center.

30. The imaging system of claim 28, wherein the first pair of x-ray sources and the second pair of x-ray sources are located below the first imaging center and the second imaging center, and wherein the pair of x-ray detectors is located above the first imaging center and the second imaging center.

31. An imaging system, comprising:
a pair of movable x-ray sources to generate a first x-ray beam and a second x-ray beam at a first separation in an imaging plane, the first x-ray beam and the second x-ray beam disposed to intersect at a first angle at a first imaging center, the pair of x-ray sources to generate a third x-ray beam and a fourth x-ray beam at a second separation in the imaging plane, the third x-ray beam and the fourth x-ray beam disposed to intersect at a second angle at a second imaging center, wherein the first imaging center and the second imaging center are different imaging centers; and
a pair of x-ray detectors at a third separation in the imaging plane, comprising a first x-ray detector and a second x-ray detector, the first x-ray detector to detect the first x-ray beam and the third x-ray beam, the second x-ray detector to detect the second x-ray beam and the fourth x-ray beam.

32. The imaging system of claim 31, wherein the pair of movable x-ray sources is located above the first imaging center and the second imaging center, and wherein the pair of x-ray detectors is located below the first imaging center and the second imaging center.

33. The imaging system of claim 31, wherein the pair of movable x-ray sources is located below the first imaging center and the second imaging center, and wherein the pair of x-ray detectors is located above the first imaging center and the second imaging center.

34. An imaging system, comprising:
a pair of movable x-ray sources, comprising a first x-ray source to generate a first x-ray beam and a second x-ray source to generate a second x-ray beam, at a first separation in an imaging plane, the first x-ray beam and the second x-ray beam disposed to intersect at a first angle at an imaging center, the pair of movable x-ray sources to generate a third x-ray beam and a fourth x-ray beam at a second separation in the imaging plane, the third x-ray beam and the fourth x-ray beam disposed to intersect at a second angle at the imaging center, wherein the first x-ray source and the second x-ray source are moved linearly between the first separation and the second separation; and
a pair of movable x-ray detectors, comprising a first x-ray detector and a second x-ray detector, to detect the first x-ray beam and the second x-ray beam at a third separation in the imaging plane and to detect the third x-ray beam and the fourth x-ray beam at a fourth separation in the imaging plane, wherein the first x-ray detector and the second x-ray detector are moved linearly between the third separation and the fourth separation.

35. The imaging system of claim 34, the first x-ray source to track a position of the first x-ray detector from the third separation of the pair of x-ray detectors to the fourth separation of the pair of x-ray detectors, the second x-ray source to track a position of the second x-ray detector from the third separation of the pair of x-ray detectors to the fourth separation of the pair of x-ray detectors.

36. An article of manufacture comprising:
a machine readable medium including data that, when executed by a machine, cause the machine to perform operations comprising:
establishing a first imaging center at a first location by generating a first pair of imaging beams to enable radiation treatment of a target anatomy from a first range of angles in a treatment frame of reference;
establishing a second imaging center at a second location by generating a second pair of imaging beams to enable radiation treatment of the target anatomy from a second range of angles in the treatment frame of reference, wherein the first location and the second location are different locations; and, generating control signals representative of the first and the second imaging centers.

37. The article of manufacture of claim 36, wherein establishing the first imaging center comprises generating a first imaging beam having a first axis and a second imaging beam having a second axis, the first axis and the second axis defining a first imaging plane, the second imaging beam disposed at a first angle with respect to the first imaging beam to intersect the first imaging beam at the first location.

38. The article of manufacture of claim 37, wherein establishing the second imaging center comprises generating a third imaging beam having a third axis in the first imaging plane, the third imaging beam disposed at a second angle with respect with respect to the first imaging beam to intersect the first imaging beam at the second location.

39. The article of manufacture of claim 38, wherein the third imaging beam is disposed at a third angle with respect to the second imaging beam, further comprising establishing a third imaging center at a third location comprising an intersection of the second imaging beam and the third imaging beam in the first imaging plane.

40. The article of manufacture of claim 37, wherein establishing the second imaging center comprises generating a third imaging beam having a third axis and a fourth imaging beam having a fourth axis, the third axis and the fourth axis defining a second imaging plane, the fourth imaging beam disposed at a second angle with respect to the third imaging beam to intersect the third imaging beam at the second location.

41. The article of manufacture of claim 40, wherein the first imaging plane and the second imaging plane are coplanar planes.

42. The article of manufacture of claim 40, wherein the first imaging plane and the second imaging plane are non-coplanar planes.

43. The article of manufacture of claim 38, the method further comprising: positioning the target anatomy at approximately the first imaging center;
generating a first image with the first imaging beam and a second image with the second imaging beam;
registering the first image and the second image with a first plurality of reference images to obtain a first registration result;
positioning a radiation treatment source with the first registration result; and
delivering radiation treatment to the target anatomy from a first range of angles.

44. The article of manufacture of claim 43, wherein the machine readable medium further includes data that cause the machine to perform operations comprising:
positioning the target anatomy at approximately the second imaging center;
generating a third image with the third imaging beam and a fourth image with the first imaging beam;
registering the third image and the fourth image with a second plurality of reference images to obtain a second registration result;
positioning the radiation treatment source with the second registration result; and
delivering radiation treatment to the target anatomy from a second range of angles.

45. The article of manufacture of claim 39, wherein the machine readable medium further includes data that cause the machine to perform operations comprising:
positioning the target anatomy at approximately the third imaging center;
generating a first image with the second imaging beam and a second image with the third imaging beam;
registering the first image and the second image with a plurality of reference images to obtain a registration result;
positioning a radiation treatment source with the registration result; and
delivering radiation treatment to the target anatomy from a third range of angles.

46. The article of manufacture of claim 40, wherein the machine readable medium further includes data that cause the machine to perform operations comprising:
positioning the target anatomy at approximately the first imaging center;
generating a first image with the first imaging beam and a second image with the second imaging beam;
registering the first image and the second image with a first plurality of reference images to obtain a first registration result;

positioning a radiation treatment source with the first registration result; and delivering radiation treatment to the target anatomy from a first range of angles.

47. The article of manufacture of claim 46, wherein the machine readable medium further includes data that cause the machine to perform operations comprising:

positioning the target anatomy at approximately the second imaging center;

generating a third image with the third imaging beam and a fourth image with the fourth imaging beam;

registering the third image and the fourth image with a second plurality of reference images to obtain a second registration result;

positioning the radiation treatment source with the second registration result; and delivering radiation treatment to the target anatomy from a second range of angles.

48. A system, comprising:

means for imaging a radiation target located at a plurality of different imaging centers to provide access to the radiation target from a plurality of treatment angles;

means for positioning the radiation target at the plurality of imaging centers; and means for delivering radiation treatments from the plurality of treatment angles.

* * * * *

UNITED STATES PATENT AND TRADEMARK OFFICE
CERTIFICATE OF CORRECTION

PATENT NO. : 7,302,033 B2  Page 1 of 1
APPLICATION NO. : 11/170832
DATED : November 27, 2007
INVENTOR(S) : Aaron Carrano et al.

It is certified that error appears in the above-identified patent and that said Letters Patent is hereby corrected as shown below:

Column 2
Line 24, delete "CyberKnife®" and substitute -- CYBERKNIFE® --.

Column 4
Line 7, delete "CyberKnife®" and substitute -- CYBERKNIFE® --.

COLUMN 5
Line 21, delete "320" and substitute --318--.

Signed and Sealed this

Sixteenth Day of September, 2008

JON W. DUDAS
*Director of the United States Patent and Trademark Office*